(12) United States Patent
Hossainy et al.

(10) Patent No.: US 6,379,381 B1
(45) Date of Patent: Apr. 30, 2002

(54) POROUS PROSTHESIS AND A METHOD OF DEPOSITING SUBSTANCES INTO THE PORES

(75) Inventors: Syed F. A. Hossainy, Fremont; Li Chen, San Jose, both of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/390,069

(22) Filed: Sep. 3, 1999

(51) Int. Cl.⁷ .................................................. A61F 2/06
(52) U.S. Cl. ..................... 623/1.42; 623/1.43; 623/1.15; 623/23.7
(58) Field of Search .................... 623/1.4, 1.42, 623/1.39, 1.43, 23.73

(56) References Cited

U.S. PATENT DOCUMENTS

| | | | |
|---|---|---|---|
| 4,459,252 A | * 7/1984 | MacGregor | 264/46.9 |
| 5,059,211 A | 10/1991 | Stack et al. | 606/198 |
| 5,163,952 A | 11/1992 | Froix | 623/1 |
| 5,306,286 A | 4/1994 | Stack et al. | 606/198 |
| 5,527,337 A | 6/1996 | Stack et al. | 606/198 |
| 5,700,286 A | 12/1997 | Tartaglia et al. | 623/1 |
| 5,713,949 A | 2/1998 | Jayaraman | 623/1 |
| 5,766,710 A | 6/1998 | Turnlund et al. | 428/36.1 |
| 5,769,883 A | 6/1998 | Buscemi et al. | 623/1 |
| 5,843,172 A | 12/1998 | Yan | 623/1 |
| 5,873,904 A | 2/1999 | Ragheb et al. | 623/1 |
| 6,120,536 A | 9/2000 | Ding et al. | 623/1.43 |
| 6,120,847 A | 9/2000 | Yang et al. | 427/335 |
| 6,206,915 B1 | * 3/2001 | Fagan et al. | 623/1.42 |

FOREIGN PATENT DOCUMENTS

| | | | |
|---|---|---|---|
| EP | 0 850 651 A3 | 1/1998 | A61L/27/00 |
| EP | 0 850 651 A2 | 1/1998 | A61L/27/00 |
| EP | 0 875 218 A3 | 4/1998 | A61F/2/06 |
| EP | 0 875 218 A2 | 4/1998 | A61F/2/06 |
| JP | 11299901 | 2/1999 | A61M/29/02 |
| WO | WO 90/01969 | 3/1990 | |
| WO | WO 98/23228 | 6/1998 | |
| WO | WO 99/16386 | 4/1999 | A61F/2/06 |

* cited by examiner

Primary Examiner—David J. Isabella
Assistant Examiner—Urmi Chattopadhyay
(74) Attorney, Agent, or Firm—Cameron Kerrigan Squire, Sanders and Dempsey, L.L.P.

(57) ABSTRACT

An implantable prosthesis, for example a stent, is provided that is capable of being loaded with substances. In one example, the prosthesis is a cylindrical-shaped body having depots or pores formed thereon. The depots can be formed at preselected locations on the body of the prosthesis and can have a preselected depth, size, and shape. The depots can have various shapes including a cylindrical or a conical shape. Substances such as therapeutic substances, polymeric materials, polymeric materials containing therapeutic substances, radioactive isotopes, and radiopaque materials can be deposited into the depots.

21 Claims, 2 Drawing Sheets

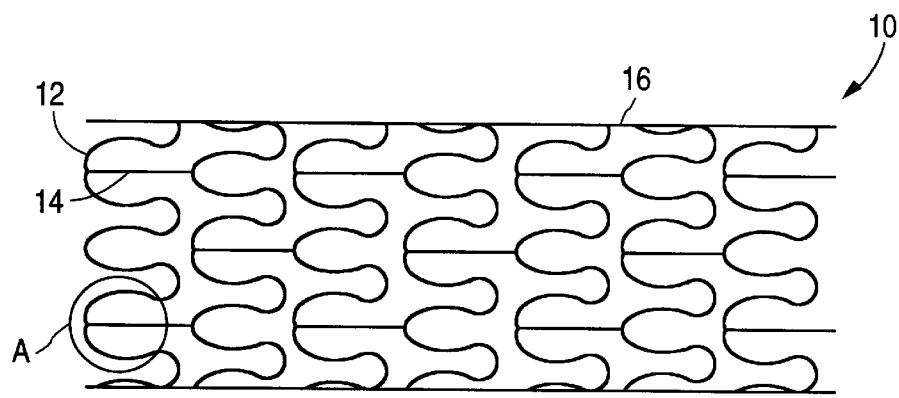
Fig. 1
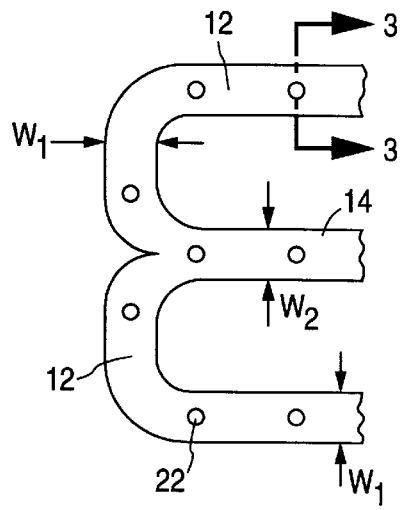
Fig. 2
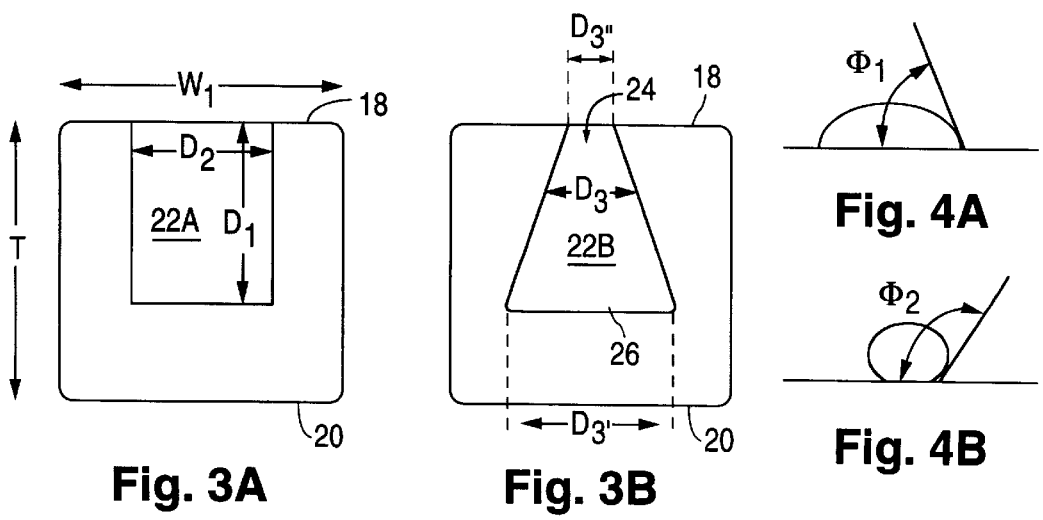
Fig. 3A    Fig. 3B    Fig. 4A
Fig. 4B

POROUS PROSTHESIS AND A METHOD OF DEPOSITING SUBSTANCES INTO THE PORES

BACKGROUND OF THE INVENTION

1. Field of the Invention

This invention relates to implantable devices, such as an expandable, intraluminal prosthesis commonly known as a stent. More particularly, this invention relates to a prosthesis having pores formed in its cylindrical body. Moreover, the present invention relates to a method of depositing substances, such as therapeutic substances, in the pores.

2. Description of the Background

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion to remodel the vessel wall. The balloon is then deflated to a smaller profile to allow the catheter to be withdrawn from the patient's vasculature.

A problem associated with the procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an intraluminal prosthesis, an example of which includes an expandable stent, is implanted in the lumen to maintain the vascular patency. Stents are scaffoldings, usually cylindrical or tubular in shape, functioning to physically hold open, and if desired, to expand the wall of the passageway. Typically stents are capable of being compressed for insertion through small cavities via small catheters, and then expanded to a larger diameter once at the desired location. Examples in patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

In treating the damaged vasculature tissue and to further fight against thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of such medication often produces adverse or toxic side effects for the patient. Local delivery is a highly suitable method of treatment in that smaller levels of medication, as compared to systemic dosages, are concentrated at a specific site. Local delivery produces fewer side effects and achieves more effective results.

One commonly applied technique for the local delivery of the drugs is through the use of medicated stents. One proposed method of medicating stents is to seed the stent with endothelial cells (Dichek, D. A. et al. Seeding of Intravascular Stents With Genetically Engineered Endothelial Cells; Circulation 1989; 80: 1347–1353). Briefly, endothelial cells can be seeded onto stainless steel stents and grown until the stents are covered. The cells are therefore able to be delivered to the vascular wall to provide therapeutic proteins. Another proposed method of providing therapeutic substances to the vascular wall includes simple heparin-coated metallic stent, whereby a heparin coating is ionically or covalently bonded to the stent. Disadvantages associated with the aforementioned methods include significant loss of the therapeutic substance from the body of the stent during delivery and expansion of the stent and an absolute lack of control of the release rate of the therapeutic substance from the stent. Another proposed method involves the use of a polymeric carrier coated onto the body of the stent, as disclosed in U.S. Pat. No. 5,464,650 issued to Berg et al., U.S. Pat. No. 5,605,696 issued to Eury et al., U.S. Pat. No. 5,865,814 issued to Tuch, and U.S. Pat. No. 5,700,286 issued to Tartaglia et al. Obstacles often encountered with the use of a polymeric coating include difficulties in coating a complicated geometrical structure, poor adhesion of the polymeric coating to the surface of a stent, and biocompatibility of the polymer. Accordingly, it is desirable to be able to secure the therapeutic substance directly onto the body of the stent. Not withstanding the benefits gained by securing a therapeutic substance to the body of the stent, it is also desirable to be able to secure other substances to the body of the stent, such as radiopaque materials, used to assist a physician to guide and deploy the stent at the proper site of treatment.

SUMMARY OF THE INVENTION

In accordance with various aspects of the present invention, an implantable prosthesis, one example of which includes a stent, is provided that is capable of being loaded with substances. The prosthesis is defined by a cylindrical shaped body having a thickness. Depots or pores are formed on the body at preselected locations. The depots have a preselected depth and shape. The depth of the depots can be equal to about 10% to about 90% of the thickness. In one embodiment, the depots can have a cylindrical shape. In another embodiment, the shape can be generally conical. Substances such as therapeutic substances, polymeric material, polymeric material containing therapeutic substances, radioactive isotopes, and radiopaque material can be deposited into the depots.

Another aspect of the present invention is a method of loading a substance into the depots. The method is applicable not only to the above-described prosthesis, but to any type of porous prosthesis. A first fluid having a substance added therein is applied to a porous prosthesis. During the application, the first fluid containing the substance is capable of penetrating into the pores. The first fluid is removed, for example by evaporation, and a second fluid is applied to the prosthesis. During the application of the second fluid, the second fluid is not capable of significantly penetrating into the pores. The second fluid can have a contact angle greater than about 90°. Contact angle is defined as the angle at the tangent of the fluid phase that has taken an equilibrium shape on a solid surface. In one embodiment of the present invention, the second fluid rinses the substance from the surface of the body of the prosthesis. In another embodiment, a therapeutic substance and/or a polymer can be added to the second fluid to form a coating of a therapeutic substance and/or polymer onto the surface of the body of the prosthesis.

In accordance to another embodiment, prior to the application of the second fluid, the prosthesis can be immersed in a third fluid and agitated via mechanical perturbation techniques. Accordingly, any of the substance gathered on the surface of the body after the application of the first fluid is removed. The third fluid should not be capable of dissolving the substance. The third fluid can have a contact angle above 90°.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

FIG. 1 is a side view of a conventional intraluminal prosthesis, the body of the prosthesis being defined by cylindrical elements engaged to one another by connecting elements;

FIG. 2 is an enlarged view of section A of FIG. 1, illustrating a portion of the cylindrical elements and connecting elements;

FIG. 3A is a cross sectional view of the cylindrical element, taken in the direction of the arrows and along the plane of line 3—3 of FIG. 2, illustrating a depot formed in the body of the prosthesis in accordance to one embodiment of the present invention;

FIG. 3B is a cross sectional view of the cylindrical element, taken in the direction of the arrow and along the plane of line 3—3 of FIG. 2, illustrating a depot formed in the body of the prosthesis in accordance to another embodiment of the present invention;

FIG. 4A illustrates a fluid on a solid surface having a contact angle $\phi_1$;

FIG. 4B illustrates a fluid on a solid surface having a contact angle $\phi_2$.

DETAILED DESCRIPTION OF THE PREFERRED EMBODIMENTS

Figure 5:
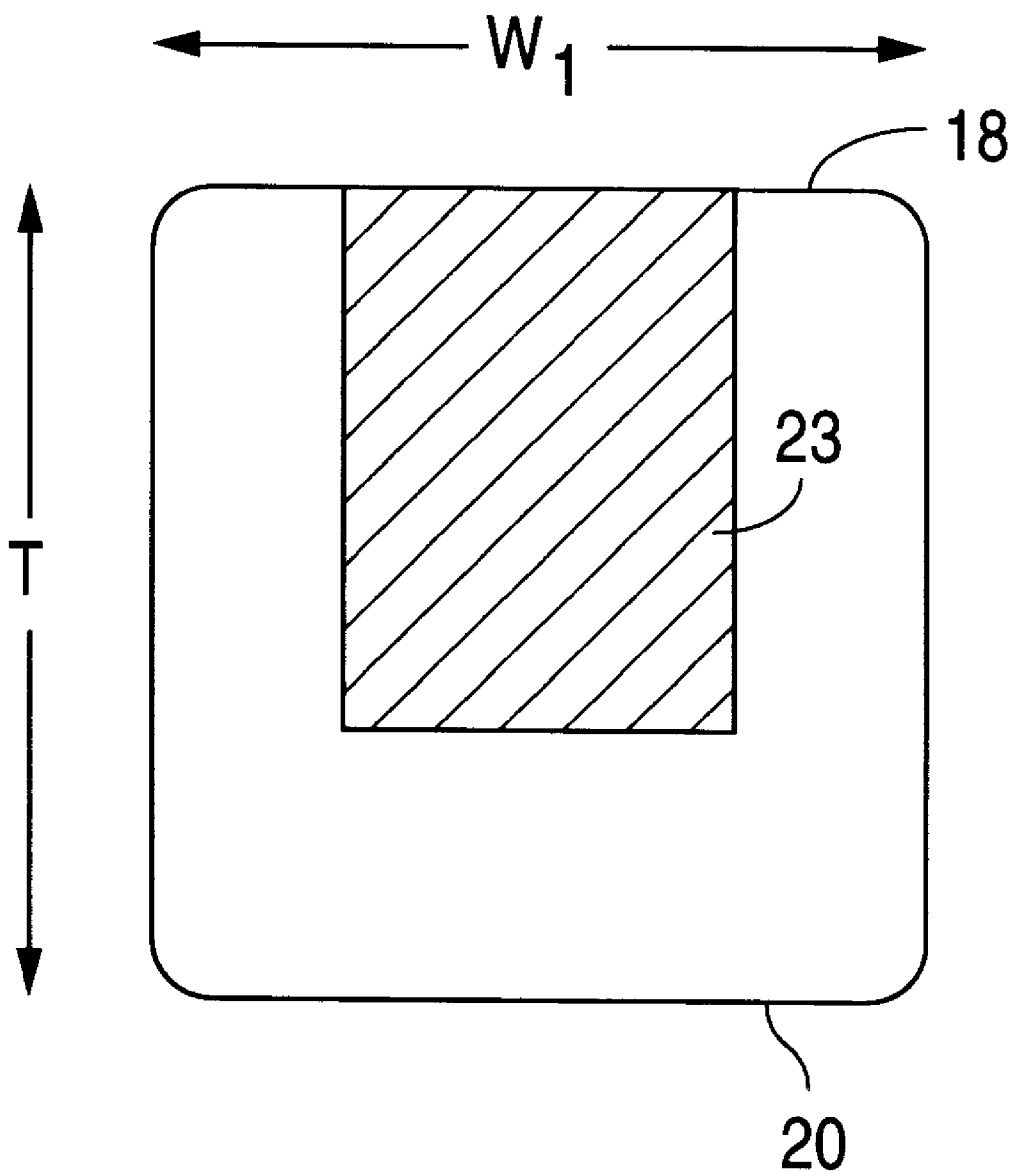
FIG. 5 is a cross sectional view of the cylindrical element, taken along the plane of line 3—3 of FIG. 2, illustrating a depot formed in the body of the prosthesis and a substance loaded in said depot in accordance with one embodiment of the present invention.

FIG. 1 illustrates an implantable prosthesis 10, one example of which includes a stent. Stents are scaffoldings, usually cylindrical or tubular in shape, that are inserted into an anatomical passageway and operate to physically hold open and, if desired, to expand the wall of a passageway. Stents are capable of being compressed for insertion through small cavities via balloon-catheters, positioned in a desired location, then expanded to a larger diameter.

In one example, illustrated in FIGS. 1 and 2, stent 10 includes a plurality of rigid but resiliently flexible thread elements 12 that are arranged in a sinusoid-like configuration that is connected to form a continuous ring or cylinder. The plurality of cylindrical thread elements 12 are radially expandable, disposed coaxially, and interconnected by connecting elements 14 that are disposed between adjacent cylindrical thread elements 12, leaving gaps or lateral openings between adjacent cylindrical thread elements 12. Although the thread elements 12 are illustratively shown in the form of cylinders or rings connected axially-displaced in-parallel, other configurations, such as helices, coils, or braids, and other connections may be utilized. Thread elements 12 and connecting elements 14 define a tubular stent body 16 having a lumen contacting surface 18 and an inner surface 20 as shown in FIGS. 3A and 3B.

Thread elements 12 have any suitable width $W_1$, typically in a range of widths $W_1$ from about 0.002 inches to about 0.006 inches. A common width $W_1$ is about 0.003 inches. Connecting elements 14 have any suitable width $W_2$, typically in a range of widths $W_2$ from about 0.002 inches to about 0.008 inches. A common width $W_2$ is about 0.005 inches. Additionally, thread elements 12 have any suitable thickness T, typically a thickness T in a range from about 0.002 inches to about 0.008 inches. A common thickness T is about 0.005 inches. Connecting elements 14 have any suitable thickness, typically in a range from about 0.002 inches to about 0.008 inches. A common connecting element 14 thickness is about 0.005 inches. A specific choice of width and thickness depends on the anatomy and size of the target lumen. In other words, the size of the stent can vary according to the intended procedure, anatomy, and usage.

In one embodiment, thread elements 12 and connecting elements 14 are typically fabricated from a metallic material or an alloy such as stainless steel (e.g., 316L), "MP35N," "MP20N," tantalum, nickel-titanium alloy (commercially available as Nitinol™), platinum-iridium alloy, gold, magnesium, or combinations of alloys. "MP35N" and "MP20N" are trade names for alloys of cobalt, nickel, chromium and molybdenum available from standard Press Steel Co., Jenkintown, Pa. "MP35N" has a nominal composition of 35% cobalt, 35% nickel, 20% chromium, and 10% molybdenum. "MP20N" has a nominal composition of 50% cobalt, 20% nickel, 20% chromium, and 10% molybdenum. The aforementioned list is merely a useful list of materials and other materials are proven to function effectively.

A single depot or pore 22 or plurality of depots or pores 22 are formed as a laser trench or laser trenches on body 16 of stent 10 by exposing surface 18 to an energy discharge from a laser, such as an excimer laser. Alternative methods of forming depots 22 include physical or chemical etching techniques. Techniques of laser fabrication or etching to form depots 22 are well-known to one of ordinary skill in the art. Depots 22 can be formed in virtually any stent structure and not merely the above-described structure. Depots 22 are used for carrying a variety of substances including but not limited to therapeutic substances, polymers impregnated with therapeutic substances, radioactive isotopes, and radiopaque materials. The locations of depots 22 vary according to the intended usage and application of stent 10. Depots 22 are formed by a manufacturer at any preselected location and have any preselected depth, size, and geometrical configuration. In one example, depots 22 are evenly distributed through body 16 and have an equal volume so that the tissue in contact with stent 10 receives an equal distribution of a therapeutic substance. Depth $D_1$ of depots 22 typically is varied in proportion to the thickness T of body 16 as well as the clinical purpose and usage.

For a stent 10 that carries a therapeutic substance or a polymeric carrier impregnated with a therapeutic substance, a suitable depot or pore depth $D_1$ has a range from about 10% to about 90% of thickness T. Typically, a depth not greater than about 50% of thickness T is most suitable. The specific depth $D_1$ of depots 22 depends on the amount of therapeutic substance that is to be deposited in depots 22. In an example of stent 10 carrying a radioactive isotope, depth $D_1$ is typically about 10% to about 80% of thickness T. A more specific suitable depth $D_1$ is not greater than about 30% of thickness T.

For a stent 10 that carries a radiopaque material, a suitable depot or pore depth $D_1$ has a range from about 10% to about 90% of thickness T. Typically, a depth not greater than about 65% is most suitable. A depth $D_1$ greater than about 65% of thickness T may compromise the structural integrity and mechanical functionality of stent 10. However the upper limit of depth $D_1$ varies depending on the material characteristics such as the hardness of the body 16.

Depots 22 may be formed in a variety of selected geometrical shapes. Referring to FIG. 3A, depot 22A has a generally cylindrical shape. A diameter $D_2$ of cylindrical depot 22A typically has a range from about 10% to about 90% of width $W_1$ or $W_2$, although the diameter $D_2$ is usually not greater than about 80% of width $W_1$ or $W_2$. The specific diameter $D_2$ depends on the application and purpose of depots 22. The upper limit of diameter $D_2$ varies depending on the material characteristics such as the hardness of the body 16.

An alternative example of a depot 22B, illustrated in FIG. 3B, is generally conical in shape. Conical shaped depot 22B has an open end 24 and a closed end 26. The open end 24 is the end that contacts a surface of a tissue. A diameter $D_3$ of conical shaped depot 22B is shown to decrease from closed end 26 to open end 24. The largest diameter $D_3'$ at the closed end 26 of conical shaped depot 22B has a range from about 10% to about 80% of width $W_1$ or $W_2$. Generally, the largest diameter $D_3'$ is not greater than about 70% of width $W_1$ or $W_2$. The smallest diameter $D_3''$ at the open end 24 of conical shaped depot 22B has a range from about 5% to about 70% of width $W_1$ or $W_2$. Generally, the smallest diameter $D_3''$ is not greater than about 60% of width $W_1$ or $W_2$. The reduced size of opening 24 of conical shaped depot 22B, as compared to that of the cylindrical shaped depot 22A, reduces the rate at which a therapeutic substance is released once the stent is implanted at the desired location of treatment. The depots 22 can have a variety of other geometrical shapes, such as elongated trenches (not illustrated).

The depth $D_1$ and diameters $D_2$ and $D_3$ of the individual depots 22 formed on body 16 of stent 10 can vary relative to one another. In one example, the manufacturer selectively controls the volume of depots 22 on different positions of body 16, either by selectively varying the volume or making the volume consistent throughout body 16. For some applications, consistent depot 22 volume is important for delivery of a therapeutic substance to insure that the substance is evenly distributed throughout stent 10 and results in consistent application of the therapeutic substance to the tissues in contact with surface 18 of stent 10.

A factor for determining the size, geometry, and concentration of depots 22 is the overall porosity of stent 10. Porosity is the total volume of pores in the body 16 of stent 10 divided by the total volume of structural material of stent 10. Porosity determines the capacity of substance that can be loaded into stent 10 of predetermined dimensions. High porosity can adversely affect the structural integrity, strength, and elasticity of stent 10. Consequently, stent design includes consideration of a tradeoff between strength, on one hand, and stent profile and stent load capacity on the other hand.

Substances are deposited into depots or pores 22 using several illustrative methods. The methods are applicable to the illustrative stent 10 described hereinbefore and also to any type of porous prosthesis. In some examples, the deposited substance is a therapeutic substance or agent such as antineoplastics, antiinflammatory substances, antiplatelets, anticoagulants, fribrinolytics, thrombin inhibitors, antimitotics, and antiproliferatives. Examples of antineoplastics include paclitaxel and docetaxel. Examples of antiplatelets, anticoagulants, fribrinolytics, and thrombin inhibitors include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antibody, recombinant hirudin, thrombin inhibitor (available from Biogen), and 7E-3B® (an antiplatelet drug from Centocore). Examples of suitable antimitotic agents include methotrexate, azathioprine, vincristine, vinblastine, flurouracil, adriamycin, and mutamycin. Examples of suitable cytostatic or antiproliferative agents include angiopeptin (a somatostatin analogue from Ibsen), angiotensin converting enzyme inhibitors such as Captopril® (available from Squibb), Cilazapril® (available from Hoffman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available from Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. While the listed therapeutic substances or agents are well known for preventative and therapeutic utility, the substances are listed by way of example and are not meant to be limiting. Other therapeutic substances which are currently available or that may be developed in the future are equally applicable. The treatment of patients using the above mentioned medicines is well-known to those of ordinary skill in the art.

In other embodiments, the therapeutic substance is a radioactive isotope for stent usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$).

A therapeutic substance is added to a first fluid or solvent. The therapeutic substance is dispersed throughout the first solvent so that it is in a true solution, saturated or supersaturated with the solvent or suspended in fine particles in the first solvent. If the therapeutic substance is suspended in particles in the first solvent, the pore size and the diameter of the opening of the pores are to be sufficiently large in comparison to the size of the particles to facilitate loading and unloading of the stent. In one example, suitable pores have a pore size that is more than ten times the particle size of a suspended therapeutic substance and an opening diameter that is more than five times the diameter of the particle size.

The first solvent can be virtually any solvent that is compatible with the therapeutic substance. A suitable first solvent typically has a high capillary permeation. Capillary permeation or wetting is the movement of fluid on a solid substrate driven by interfacial energetics. Capillary permeation is quantitated by a contact angle, defined as the angle at the tangent of the first solvent droplet in fluid phase that has taken an equilibrium shape on a solid surface. A low contact angle means a higher wetting liquid. A suitably high capillary permeation corresponds to a contact angle less than about 90°.

For example, FIG. 4A illustrates a fluid having a high capillary permeation that corresponds to a solvent contact angle $\phi_1$ less than about 90°. FIG. 4B illustrates a fluid having a low capillary permeation that corresponds to a fluid contact angle $\phi_2$ greater than about 90°. The first fluid can have a viscosity not greater than about ten centipoise at room temperature. A high capillary permeation and a viscosity not greater than about ten centipoise allows the first solvent to penetrate into the pores of the prosthesis more quickly, eliminating a requirement to apply the first solvent to the prosthesis for a prolonged period of time. The first solvent can be volatile, facilitating evaporation of the first solvent. Useful examples of some first solvent include, but are not limited to, acetone, ethanol, methanol, isopropanol, tetrahydrofuran, and ethyl acetate. The first solvent is applied to a porous prosthesis, for example by immersing or spraying the solvent in procedures that are well-known to one having ordinary skill in the art.

The first solvent is applied for a predetermined period of time, the specific time depending on the capillary permeation and viscosity of the first solvent, the volume of the pores, and the amount of substance to be deposited. Therapeutic parameters such as the concentration of the therapeutic substance in the solvent and dosages depend on the duration of local release, the cumulative amount of release, and desired rate of release. Correlations and interrelations between the therapeutic parameters are well-known to one having ordinary skill in the art and are simply calculated.

After applying the first solvent for a selected duration, the first solvent is removed from the prosthesis. In one example, the first solvent is removed by evaporation in ambient pressure, room temperature, and anhydrous atmosphere and/or by exposure to mild heat (e.g., 60° C.) under a vacuum condition. The prosthesis typically has a clustered or gross formation of a therapeutic substance gathered on the body surface. The cluster is generally removed by immersing the prosthesis in a second fluid and agitating the prosthesis via mechanical perturbation techniques, such as vortexing or vigorous shaking. The second fluid is a non-solvent so that the therapeutic substance does not significantly dissolve in the second fluid. The non-solvent can have a low capillary permeation or a contact angle greater than about 90° and a viscosity not less than about 0.5 centipoise so that the second fluid is not capable of significantly penetrating into the pores during the process of agitation. Examples of a second fluid include but are not limited to saturated hydrocarbons or alkanes, such as hexane, heptane, and octane.

The prosthesis is rinsed in a third fluid. The third fluid is typically a solvent to facilitate dissolution of the therapeutic substance. The third fluid generally has a low capillary permeation, corresponding to a contact angle greater than about 90°. The third fluid has a viscosity of not less than about 1.0 centipoise and is therefore incapable of significantly penetrating into the pores during the rinsing stage. The rinsing is conducted rapidly for example in a range from 1 second to about 15 seconds, the exact duration depending on the solubility of the therapeutic substance in the solvent. Extended duration of exposure of the third solvent to the prosthesis may lead to the penetration of the third solvent into the pores.

The rinsing step is repeated, if desired, until all traces of therapeutic substance are removed from the surface of the stent. The third fluid removes excess traces of therapeutic substance from the surface of the prosthesis body. Useful examples of third fluids include but are not limited to dimethylsulfoxide (DMSO), water, DMSO in an aqueous solution, glyme, and glycerol. The third fluid is removed from the prosthesis body using a technique such as evaporation in ambient pressure, room temperature and anhydrous atmosphere and/or by exposure to mild heat (e.g., 60° C.) under vacuum condition. The first, second, third fluids are selected to not adversely affect the characteristics and composition of the therapeutic substance.

In one embodiment, the third fluid can be highly volatile, for example having a boiling point of not greater than about 60° C. at 1 atm. Accordingly, the third fluid is capable of rapidly evaporating. Rapid evaporation of the third fluid causes the third fluid to be removed from the prosthesis prior to any significant penetration of the third fluid in the pores. A useful example of a highly volatile third fluid includes, but is not limited to, Freon (e.g., Xerosolv™).

As illustrated in FIG. 5, once loaded, substance 23 remains in the pores of the prosthesis. As a result of prosthesis deployment and expansion, the expanded prosthesis engages the wall of the anatomical passageway and the therapeutic substance may elute from the porous cavities and be absorbed into the tissue of the walls of the passageway that are in contact with the prosthesis.

In some embodiments, a surface of the stent is coated with a therapeutic substance in addition to having a therapeutic substance deposited in the pores. A coating of therapeutic substance on the surface of the prosthesis is formed by adding the therapeutic substance to the third fluid rinse. The therapeutic substance is dispersed through the third fluid to form a true solution with the third solvent, rather than a dispersion of fine particles. The therapeutic substance is a substance that is capable of absorbing or attaching to the prosthesis surface. For example, highly suitable therapeutic substances for a stainless steel prosthesis include taxol and dexamethasone that easily attach to a metallic substrate.

Suitable substances for a Nitinol™ prosthesis include aspirin and heparin. The therapeutic substance added to the third fluid can be the same substance as the therapeutic substance deposited in the pores or a different substance. Rinsing with the third fluid is optionally prolonged or repeated to increase the thickness of the prosthesis therapeutic substance coating.

In another example, a polymeric coating is formed on the surface of the prosthesis, covering the pores containing deposited therapeutic substance. The polymeric coating forms a membrane that reduces the rate of release of a therapeutic substance from the pores. A polymeric material is added to the third fluid rinse to form a coating made from the polymeric material on the prosthesis surface.

The polymeric material, by example and not limitation, forms about 1% to about 3% by weight of the total weight of the solution. The polymeric material is most suitably biocompatible, including polymers that are non-toxic, non-inflammatory, chemically inert, and substantially non-immunogenetic in the applied amounts. The polymer is typically bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable, biodegradable materials include but are not limited to polycaprolactone (PCL), poly-D, L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates. Biomolecules such as heparin, fibrin, fibrinogen, cellulose, starch, and collagen are typically also suitable. Examples of biostable polymers include Parylene®, Parylast®, polyurethane (for example, segmented polyurethanes such as Biospan®), polyethylene, polyethlyene teraphthalate, ethylene vinyl acetate, silicone and polyethylene oxide.

After the evaporation of the third solvent, a polymeric layer remains on the surface of the prosthesis and over the pores. The polymeric coating is alternatively formed by other conventional methods such as plasma polymerization, the practice of which is well known to one of ordinary skill in the art.

In another example, the aforementioned polymeric coating is impregnated with a therapeutic substance that is added to the third fluid-polymer mixture. Concentration of the therapeutic substance depends on release parameters including the duration of local release, the cumulative amount of release, and the desired rate of release. The correlations and interrelations between the release parameters are well-known to those of ordinary skill in the art and easily calculated. The polymeric material, by example and not limitation, makes up from about 1% to about 3% by weight of the total weight of the solution. The therapeutic substance, by example and not limitation, typically makes up about 0.3% to about 1% of the total weight of the solution. Once the third solvent is evaporated, a polymeric coating impregnated with a therapeutic substance remains on the surface, covering the therapeutic substance-filled pores.

In another example, a polymeric material, such as any of the polymeric materials listed herein, is impregnated with a therapeutic substance and deposited into the pores. The polymeric material reduces the rate of release of the therapeutic substance from the pores. The method of application includes adding a therapeutic substance and a polymer to a first fluid or solvent. The therapeutic substance is dispersed throughout the first solvent to dissolve into a true solution, or is saturated or supersaturated with the solvent or suspended in fine particles in the first solvent. The polymeric material is also dispersed throughout the first solvent to form a true solution, or is suspended in fine particles in the first solvent. Saturation or supersaturation of the polymer is less suitable since the viscosity of the first solvent is raised beyond a desired limit.

If the therapeutic substance is suspended in the first solvent, the pore size and the diameter of the opening of the pores are to be sufficiently large in comparison to the size of the particles to facilitate loading and unloading of the stent. In one example, suitable pores have a pore size that is more than ten times the particle size of a suspended therapeutic substance and an opening diameter that is more than five times the diameter of the particle size.

The first solvent is selected from among solvents that are compatible with the polymer and therapeutic substance. A first solvent having a high capillary permeation or a contact angle not higher than about 90° improves performance. The first solvent can have a viscosity not higher than about ten centipoise. The first solvent can be volatile to facilitate evaporation. Useful examples of a first solvent include but are not limited to acetone, ethanol, methanol, isopropanol, tetrahydrofuran, and ethyl acetate. The first solvent is applied to a porous prosthesis, by for example, immersing or spraying. The first solvent is applied for a predetermined time period, the specific time depending on the capillary permeation and viscosity of the first solvent, volume of the pores, and the amount of substance to be deposited. Therapeutic parameters such as the concentration of the therapeutic substance and the specific polymer depend on the duration of local release, the cumulative amount of release, and the rate of release that is desired. Correlations and interrelations between the therapeutic parameters are well-known to those having ordinary skill in the art and are easily determined.

After a selected time duration, the first solvent is removed from the prosthesis by a technique such as evaporation in ambient pressure, room temperature, and anhydrous atmosphere and/or by exposure to mild heat (e.g., 60° C.) under vacuum condition. The prosthesis typically has a cluster of polymeric material and therapeutic substance formed on the body surface. The cluster is removed by immersing the prosthesis in a second fluid and agitating the prosthesis via mechanical perturbation techniques, such as vortexing or vigorous shaking. The second fluid is a non-solvent so that the therapeutic substance and the polymer are not capable of dissolution in the second fluid. The non-solvent generally has a low capillary permeation, corresponding to a contact angle greater than about 90° and a viscosity not less than 0.5 centipoise so that the second fluid is not capable of significantly penetrating into the pores during the process of agitation. Examples of the second fluid include but are not limited to saturated hydrocarbons or alkanes, such as hexane, heptane, and octane.

The prosthesis is rinsed in a third fluid subsequent to the application of the first solvent or the agitation of the prosthesis. The third fluid typically has a low capillary permeation, corresponding to a contact angle greater than about 90°. The third fluid has a viscosity of not less than 1.0 centipoise. The third fluid is not capable of significantly penetrating into the pores during the rising stage. In one embodiment, the third fluid is capable of significantly dissolving both the therapeutic substance and the polymeric material. Rinsing is conducted rapidly for example for a duration in a range from 1 second to about 15 seconds. The specific duration depends on the solubility of the therapeutic substance and the polymeric material characteristics. The rinsing is repeated, if desired, until all traces of therapeutic substance and polymeric material are removed from the stent surface.

In an alternative embodiment, the third fluid is capable of significantly dissolving the therapeutic substance but not the polymeric material. As a result, traces of therapeutic substance are removed from the surface of the prosthesis, leaving a polymeric coating covering the surface of the prosthesis including the pores. The polymeric coating serves as an additional rate-reducing membrane. Useful examples of third fluid include but are not limited to DMSO, water, DMSO in an aqueous solution, and glycerol. The third fluid can be removed from the body of the prosthesis using a technique such as evaporation in ambient pressure, room temperature and anhydrous atmosphere and/or by exposure to mild heat (e.g., 60° C.) under vacuum condition. The first, second, third fluids, alone or in conjunction with the polymeric material should not adversely affect the characteristics and composition of the therapeutic substance.

In another example, a polymeric material, such as a material capable of swell-loading or post-loading, can be deposited into the pores. Swell-loading occurs when a polymeric carrier is soaked with a therapeutic substance/solvent solution. The polymer swells, receiving the therapeutic substance in the polymer matrix. Once the solvent is removed, the polymer collapses and is impregnated with the therapeutic substance. Examples of polymeric material that are susceptible to swell-loading include thermoplastic polymers such as polyurethanes, polylactic acid, and polyglycolic acid, and non-thermoplastic polymers such as polyethyleneglycol, polyvinyl alcohol, polyacrylamide, tecophilic polymers and crosslinked configurations thereof. The method of depositing a polymeric material into the pores is generally similar to the above-described methods with an addition of a curing step for the non-thermoplastic polymers subsequent to the rinsing step. One of ordinary skill in the art of polymer fabrication understands how to cure a non-thermoplastic polymer.

In another example, a radiopaque substance such as gold is deposited into the pores. The process of depositing radioactive isotopes is generally similar to the methods described above with a radiopaque substance dispersed and suspended in fine particles through a first fluid. The first fluid can have a high capillary permeation or a contact angle not higher than about 90°. The first fluid has a viscosity not higher than about ten centipoise and can be volatile, ensuring that the first fluid evaporates more readily and easily. Useful examples of first fluids include acetone, ethanol, methanol, isopropanol, tetrahydrofuran, and ethyl acetate.

The first fluid is applied to a porous prosthesis for a predetermined period of time, typically about 30 minutes. After application, the first solvent is removed from the prosthesis using a technique such as evaporation in ambient pressure, room temperature, and anhydrous atmosphere and/ or by exposure to mild heat (for example, 60° C.) under vacuum condition. The prosthesis may have a gross formation of radiopaque substance gathered on the prosthesis body surface. The radiopaque formation can be removed by immersing the prosthesis in a second fluid and agitating the prosthesis via mechanical perturbation techniques, such as vortexing or vigorous shaking. The second fluid can have a low capillary permeation or a contact angle greater than about 90° and a viscosity not less than about 0.5 centipoise so that the second fluid is not capable of significantly penetrating into the pores during the process of agitation. Examples of the second fluid include but are not limited to saturated hydrocarbons or alkanes, such as hexane, heptane, and octane.

The prosthesis is rinsed in a third fluid subsequent to the application of the first fluid or the agitation of the prosthesis. The third fluid has a low capillary permeation or a contact angle greater than about 90°, and has a viscosity not less than about 1.0 centipoise so that the third fluid is not capable of significantly penetrating into the pores during the rinsing stage. The rinsing is conducted rapidly, for example in a range from 1 second to about 15 seconds, since an extended exposure duration may result in penetration of the third fluid into the pores. Suitable materials for the third fluid include DMSO, water, glyme and glycerol. Rinsing is repeated, if desired, until all traces of radiopaque substance are removed from the surface of the stent. The third fluid is removed from the body of the prosthesis using a technique such as evaporation in ambient pressure, room temperature and anhydrous atmosphere or by exposure to mild heat (e.g., 60° C.) under vacuum condition. Sintering of the radiopaque material deposited in the pores is performed to bond particles of the radiopaque material without melting the particles. Appropriate pressure and temperature of radiopaque material sintering is specific to the particular material in a manner well known to one having ordinary skill in the art.

Several examples illustrate various methods for depositing substances such as therapeutic substances on a stent. The examples illustrate but do not limit the possible techniques for depositing substances.

EXAMPLE 1

Trapidil is dissolved in ethanol by conventional methods. Trapidil makes up about 15% by weight of the total weight of the solution. A stent having a porous surface is immersed in the solution for 30 minutes. The stent is removed and mounted on a mandrel at ambient pressure, room temperature, and anhydrous atmosphere for approximately 30 minutes, until the ethanol is evaporated. The stent is submerged in hexane, followed by mechanical perturbation in a vortex apparatus for about 15 seconds. The stent is removed from the non-solvent and rinsed with water for about 5 seconds. The stent is dried at ambient pressure, room temperature, and anhydrous atmosphere.

EXAMPLE 2

Trapidil is dissolved in ethanol by conventional methods. Trapidil makes up about 20% by weight of the total weight of the solution. A stent having a porous surface is immersed in the solution for 20 minutes. The stent is removed and mounted on a mandrel at ambient pressure, room temperature, and anhydrous atmosphere for approximately 30 minutes, until the ethanol is evaporated. The stent is submerged in heptane, followed by mechanical perturbation in vortex apparatus for 45 seconds. The stent is removed from the non-solvent and rinsed with dimethylsulfoxide (DMSO) for about 5 seconds. After rinsing, the mandrel is placed in ambient pressure, room temperature, and anhydrous atmosphere for approximately 2 hours, until the DMSO is evaporated.

EXAMPLE 3

Trapidil is dissolved in ethanol by conventional methods. Trapidil makes up about 25% by weight of the total weight of the solution. A stent having a porous surface is immersed in the solution for 20 minutes. The stent is removed and mounted on a mandrel at ambient pressure, room temperature, and anhydrous atmosphere for approximately 30 minutes, until the ethanol is evaporated. The stent is submerged in heptane, followed by mechanical perturbation in vortex apparatus for about 60. The stent is removed from the non-solvent and rinsed with a dimethylsulfoxide (DMSO) aqueous solution (having a 1:1 DMSO-water ratio) for about 5 seconds. After rinsing, the mandrel is placed in ambient pressure, room temperature, and anhydrous atmosphere for approximately 2 hours. Next, the prosthesis is placed in an oven under vacuum condition and at a temperature of about 60° C. for 24 hours, until all of the DMSO and water is evaporated.

EXAMPLE 4

Trapidil is dissolved in ethanol by conventional methods. Trapidil makes up about 25% by weight of the total weight of the solution. A stent having a porous surface is immersed in the solution for 30 minutes. The stent is removed and mounted on a mandrel at ambient pressure, room temperature, and anhydrous conditions for approximately 30 minutes, until the ethanol is evaporated. The stent is submerged in heptane, followed by mechanical perturbation in a vortex apparatus for about 45 seconds. The stent is removed from the non-solvent and rinsed, for about 10 seconds, with solution of ethylene vinyl alcohol and DMSO, the ethylene vinyl alcohol constituting about 1% by weight of the total weight of the solution. The mandrel is placed in ambient pressure, room temperature, and anhydrous condition for approximately 2 hours. The stent is placed in a oven under vacuum condition and at a temperature of about 60° C. for 24 hours, until all of the DMSO is evaporated. A polymeric coating remains on the surface of the stent.

EXAMPLE 5

Trapidil is dissolved in ethanol by conventional methods. Trapidil makes up about 20% by weight of the total weight of the solution. A stent having a porous surface is immersed in the solution for 40 minutes. The stent is removed and mounted on a mandrel at ambient pressure, room temperature, and anhydrous conditions for approximately 30 minutes, until the ethanol is evaporated. The stent is submerged in heptane, followed by mechanical perturbation in a vortex apparatus for about 30 seconds. The stent is removed from the non-solvent and rinsed, for about 10 seconds, with a solution containing ethylene vinyl alcohol, trapidil, and DMSO. The ethylene vinyl alcohol constitutes about 1% by weight and the trapidil constitutes about 0.33% by weight of the total weight of the solution. The mandrel is placed in ambient pressure, room temperature, and anhydrous condition for approximately 2 hours. The stent is placed in a oven under vacuum condition and at a temperature of about 60° C. for 24 hours, until all of the DMSO is evaporated. A polymeric coating having a trapidil impregnated therein remains on the stent.

EXAMPLE 6

Trapidil was dissolved in ethanol by conventional methods. Trapidil was used to make 40% by weight of the total weight of the solution. A stent having a porous surface was mounted on a mandrel and dipped in the 40% solution for 40 seconds. The stent was removed from the other end and dried at ambient pressure, room temperature, and anhydrous conditions for about 30 minutes, until the ethanol was evaporated. The stent was mounted on a mandrel again and rinsed in a heparin (DuraFlo™)/Trapidil solution for 3 seconds. The solution constituted 0.6% by weight of Heparin and 0.6% by weight of Trapidil. The solvent used was Freon (Xerosolv) and n-Propanol in the ratio of 5:1 by volume. The stent was placed in a humidity controlled chamber at room temperature for 12 hours until all of the Freon and n-Propanol solvent system evaporated. A DuraFlo coating having Trapidil impregnated therein remained on the stent surface and inside the pores.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of the invention.

What is claimed is:

1. An implantable prosthesis, comprising:
   a body structure having a generally cylindrical shape, an outer surface capable of contacting an inner lumen surface of a passageway, and a hollow bore which extends longitudinally through said body structure to define an inner surface, said body structure having a thickness;
   said body structure having a plurality of depots formed on at least a region of said outer surface, said depots having a depth less than said thickness of said body structure, and said depots having a preselected and controlled location and a preselected and controlled depth; and
   a substance deposited into said depots.

2. The implantable prosthesis of claim 1, wherein said prosthesis is a stent.

3. The implantable prosthesis of claim 1, wherein said depots are laser trenches formed by exposing said outer surface to an energy discharge from a laser.

4. The implantable prosthesis of claim 1, wherein said preselected and controlled depth is equal to about 10% to 90% of said thickness.

5. The implantable prosthesis of claim 1, wherein said preselected and controlled depth is not greater than about 65% of said thickness.

6. The implantable prosthesis of claim 1, wherein said depots have a preselected shape.

7. An implantable prosthesis, comprising:
   a body structure having a generally cylindrical shape, an outer surface capable of contacting an inner lumen surface of a passageway, and a hollow bore which extends longitudinally through said body structure to define an inner surface, said body structure having a thickness;
   said body structure having a plurality of depots formed therein, said depots having a depth less than said thickness of said body structure, and said depots having a preselected and controlled distribution, a preselected and controlled depth, and a preselected depot shape, wherein said preselected depot shape is generally conical.

8. An implantable prosthesis, comprising:
   a body structure having a generally cylindrical shape, an outer surface capable of contacting an inner lumen surface of a passageway, and a hollow bore which extends longitudinally through said body structure to define an inner surface, said body structure having a thickness;
   said body structure having a plurality of depots formed therein, said depots having a depth less than said thickness of said body structure, and said depots having a preselected and controlled distribution, a preselected and controlled depth, and a generally conical shape, wherein said conical shaped depot has an open end and a closed end, said open end contacts said inner lumen surface of said passageway, and said open end has a diameter smaller than a diameter of said closed end.

9. The implantable prosthesis of claim 8 further comprising a substance deposited into said depots.

10. The implantable prosthesis of claim 9 wherein said substance deposited into said depots is a therapeutic substance.

11. The implantable prosthesis of claim 9 wherein said substance deposited into said depots is selected from a group of antineoplastic, antiplatelet, anticoagulant, fribrinolytics, antimitotic, thrombin inhibitor, antiinflammatory, and antiproliferative substances.

12. The implantable prosthesis of claim 9 wherein said substance deposited into said depots is a radioactive isotope.

13. The implantable prosthesis of claim 9 wherein said substance deposited into said depots is a polymeric material.

14. The implantable prosthesis of claim 9 wherein said substance deposited into said depots is a radiopaque substance.

15. The implantable prosthesis of claim 8 further comprising a substance deposited into said depots, wherein said substance is a polymeric material containing a therapeutic substance.

16. An implantable prosthesis, comprising:
   a body structure having a generally cylindrical shape, an outer surface capable of contacting an inner lumen surface of a passageway, and a hollow bore which extends longitudinally through said body structure to define an inner surface, said body structure having a thickness;
   said body structure having a plurality of depots formed on at least a region of said outer surface, said depots having a depth less than said thickness of said body structure, and said depots having a preselected and controlled location and a preselected and controlled depth; and a substance deposited into said depots, wherein said substance is a polymeric material containing a therapeutic substance.

17. An implantable prosthesis, comprising:

a body structure having a generally cylindrical shape, an outer surface capable of contacting an inner lumen surface of a passageway, and a hollow bore which extends longitudinally through said body structure to define an inner surface, said body structure having a thickness;

said body structure having a plurality of depots formed on at least a region of said outer surface, said depots having a depth less than said thickness of said body structure, and said depots having a preselected and controlled location and a preselected and controlled depth; and a substance deposited into said depots, wherein said substance is a polymeric material containing a therapeutic substance, said therapeutic substance is selected from a group of antineoplastic, antiplatelet, anticoagulant, fibrinolytic, antimitotic, thrombin inhibitor, antiinflammatory, and antiproliferative substances.

18. An implantable prosthesis, comprising:

a body structure having a generally cylindrical shape, an outer surface capable of contacting an inner lumen surface of a passageway, and a hollow bore which extends longitudinally through said body structure to define an inner surface, said body structure having a thickness;

said body structure having a plurality of depots formed on at least a region of said outer surface, said depots having a depth less than said thickness of said body structure, and said depots having a preselected and controlled location and a preselected and controlled depth; and a substance in said depots, the substance being loaded in the depots by applying a first fluid including the substance to said prosthesis, wherein during said act of applying, said first fluid penetrates into said depots, removing said first fluid from said prosthesis, applying a second fluid to said prosthesis wherein during said act of applying said second fluid, said second fluid does not significantly penetrate into said depots, and removing said second fluid from said prosthesis such that said substance is deposited into said depots, wherein said substance is selected from a group of therapeutic substances, polymeric material, or a combination thereof.

19. A stent comprising:

a radially expandable body; and depots located on a selected area of the surface of said body wherein the depots are conically shaped cavities having an open end and a closed end, said open end having a dimension that is smaller than a dimension of said closed end.

20. The stent of claim 19, wherein said depots contain a substance.

21. The stent of claim 19, wherein the depots contain a substance selected from a group of antineoplastic, antiplatelet, anticoagulant, fribrinolytics, antimitotic, thrombin inhibitor, antiinflammatory, and antiproliferative substances.

* * * * *